(12) United States Patent
Mann et al.

(10) Patent No.: US 6,395,550 B1
(45) Date of Patent: May 28, 2002

(54) METHOD AND APPARATUS FOR TISSUE TREATMENT

(75) Inventors: Michael J. Mann, Newton, MA (US); Paul Cherkas, San Jose, CA (US)

(73) Assignee: Corgentech, Inc., Palo Alto, CA (US)

( * ) Notice: Subject to any disclaimer, the term of this patent is extended or adjusted under 35 U.S.C. 154(b) by 0 days.

(21) Appl. No.: 09/480,194

(22) Filed: Jan. 10, 2000

(51) Int. Cl.$^7$ ................................................ C12N 15/85
(52) U.S. Cl. ........................................................ 435/455
(58) Field of Search .................. 435/440, 455–467, 435/283.1–287.3, 285.1, 286.6, 284.1–284.3; 514/44

(56) References Cited

PUBLICATIONS

Mann et al., "Pressure–mediated Oligonucleotide Transfection of Rat and Human Cardiovascular Tissues," *Proc. Natl. Acad. Sci. USA* 96:6411–6415 (1999).

*Primary Examiner*—Remy Yucel
(74) *Attorney, Agent, or Firm*—Clark & Elbing LLP

(57) ABSTRACT

The invention provides a method and an apparatus for treating a tissue, such as a blood vessel, with therapeutic liquids, such as solutions of genes encoding therapeutic proteins.

34 Claims, 2 Drawing Sheets

METHOD AND APPARATUS FOR TISSUE TREATMENT

BACKGROUND OF THE INVENTION

This invention relates to the treatment of tissues, in particular blood vessels, with therapeutic liquids, such as solutions of genes encoding therapeutic products.

A number of surgical procedures, and in particular minimally invasive surgical procedures, involve ex vivo treatment of blood vessels and other tissues prior to introduction of the tissues into patients. An example of this is the treatment of vein or arterial grafts to be used in cardiac bypass procedures; such grafts can be rendered less susceptible to stenosis by ex vivo treatment of the grafts, prior to their introduction into patients, with therapeutic solutions, e.g., those containing genes encoding stenosis-inhibiting products (i.e., RNAs or proteins). Preferably, such treatment is carried out under pressure, as is described in U.S. Pat. Nos. 5,766,901 and 5,922,687, which are hereby incorporated by reference.

SUMMARY OF THE INVENTION

The invention provides a method and an apparatus for exposing a tissue to a treatment medium in a controlled fashion, so that treatment is conducted in an effective, efficient, and safe manner.

Accordingly, the invention features a method for treating a biological tissue (e.g., an elongate biological tissue, such as a blood vessel (e.g., a vein or an artery)) with a therapeutic liquid solution by (a) placing the tissue in an inner trough-shaped chamber; (b) inserting the resultant trough-held tissue into a closable outer chamber; (c) closing the outer chamber; and (d), before or after step (c), infusing the solution into the outer chamber (e.g., by use of a syringe) so that it contacts the tissue.

Optionally, before step (c), the inner trough-shaped chamber is removed from the outer chamber; the outer chamber is closed by means of a removable cap; or the therapeutic liquid solution in the outer chamber contacts the tissue under pressure.

The outer chamber can include or consist of an elongate tubular structure, which consists of, for example, two or more tubular segments that are reversibly hinged to one another, e.g., so as to allow flexion between the segments. The outer chamber containing the tissue and the treatment medium can be fashioned from modular components and/or be tailored to conform to the shape and/or size of the tissue, to minimize the volume requirement of the treatment medium, which can be costly, in particular where it contains DNA or other therapeutic molecules. The walls of the outer chamber can be rigid or flexible; if flexible, such flexibility can, in part, provide a means for adjusting the size and shape of the outer chamber to accommodate the tissue. The outer chamber can also be composed of a collapsible or expandable material that is extended around the tissue to achieve a conformity of size and/or shape.

Before or after step (a), one end of an elongate tissue treated according to the invention can be secured to a canula, e.g., by ligature. The canula can be removably attached to the inner trough-shaped chamber via a gripping mechanism. Also, when placed in the outer chamber with the tissue, the canula can be removably attached to one end of the outer chamber. The therapeutic liquid solution can be introduced into the outer chamber via such a canula.

To facilitate handling and manipulation of the tissue with minimal trauma or injury, the interior surface of the outer chamber and/or the surface of the inner chamber onto which the tissue is placed (herein also referred to as the introducer or trough) can be composed of a biocompatible, slippery material, having a low coefficient of friction.

The invention also includes an apparatus for treating a biological tissue with a therapeutic liquid solution, which consists of (a) a sterile outer chamber that can be closed to be fluid-tight, and that is adapted for enclosing the tissue so that it can be contacted with the solution; and (b) a sterile open inner trough-shaped chamber adapted to be inserted into the outer chamber, and further being adapted to hold the tissue for introduction of the tissue into the outer chamber.

The apparatus can also include a canula that is removably attached to the inner chamber via a gripping mechanism and that is adapted such that one end of an elongate tubular tissue can be removably attached to the canula. When placed in the outer chamber with the tissue and the inner chamber, the canula can be removably attached to one end of the outer chamber, and a cap can be used to seal the end of the outer chamber to which the canula is not attached.

Also, the outer chamber can include or consist of an elongate tubular enclosure, consisting of, for example, two or more segments that are reversibly hinged to one another, e.g., so as to allow flexion between the segments. As is noted above, the outer chamber containing the tissue and the treatment medium can be fashioned from modular components and/or be tailored to conform to the shape and/or size of the tissue, to minimize the volume requirement of the treatment medium, which can be costly, in particular where it contains DNA or other therapeutic molecules. The walls of the outer chamber can be rigid or flexible; if flexible, such flexibility can, in part, provide a means for adjusting the size and shape of the outer chamber to accommodate the tissue. The outer chamber can also be composed of a collapsible or expandable material that is extended around the tissue to achieve a conformity of size and/or shape.

The apparatus can also include a means for altering the pressure in the outer chamber; a syringe for introducing the therapeutic liquid solution into the outer chamber or for altering the pressure in the outer chamber; a device for monitoring the pressure within the outer chamber; a mechanism for automated pressurization of, or delivery of fluid into, the outer chamber; or a feedback mechanism for regulating the pressure, fluid volume, temperature, or oxygen content of the outer chamber.

As is noted above, to facilitate handling and manipulation of the tissue with minimal trauma or injury, the interior surface of the outer chamber and/or the surface of the inner chamber onto which the tissue is placed can be composed of a biocompatible, slippery material, having a low coefficient of friction. Finally, the walls of the outer chamber can be clear, so that the treatment of the biological tissue can be monitored visually.

Other features and advantages of the invention will be apparent from the following detailed description, drawings, and claims.

DESCRIPTION OF THE PREFERRED EMBODIMENTS

Figure 1:
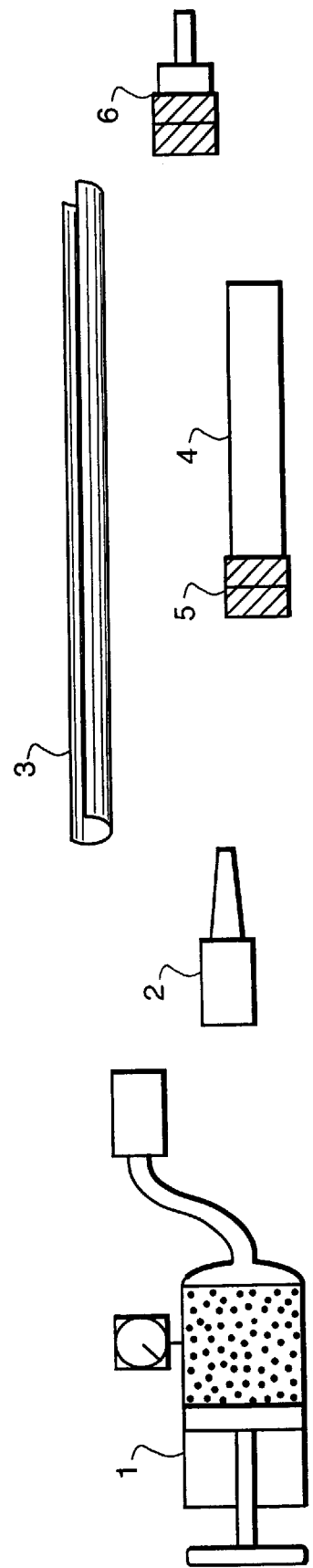
FIG. 1 is a diagrammatic representation of the components of an apparatus of the invention.

Referring to FIG. 1, the components of one embodiment of a tissue treatment apparatus of the invention are illustrated diagrammatically. These include syringe (1), containing the treatment fluid; canula (2); introducer (3); chamber tube (4), including joint (5); and cap (6).

Figure 2:
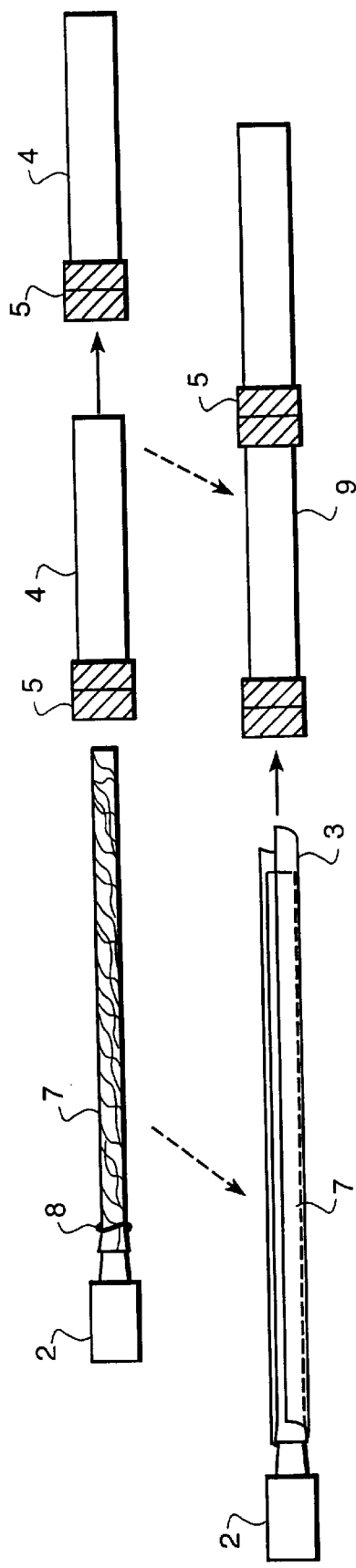
FIG. 2 is a diagrammatic representation of the steps followed in putting together the components of an apparatus of the invention.
Figure 3:
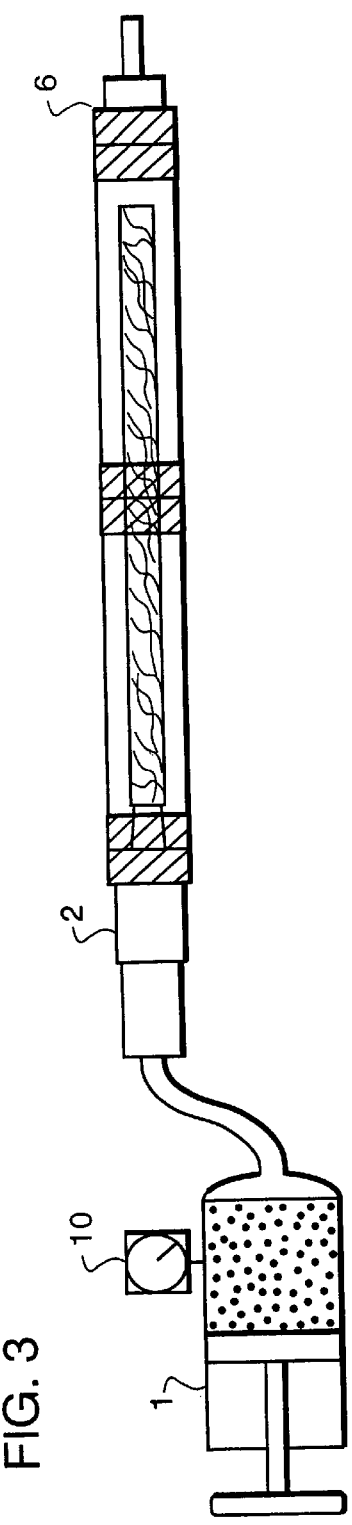
FIG. 3 is a diagrammatic representation of the components of an apparatus of the invention in operation.

Referring to FIGS. 2 and 3, the blood vessel (7) to be treated is mounted on canula (2) and secured with ligature (8). The vessel is placed on introducer (3), which can be temporarily attached to the canula via a gripping mechanism. The free end of the introducer is then passed into tubular chamber (9). This chamber is comprised of tubular components (4) that can be connected with fluid-tight and/or pressure-limiting joints (5); by varying the number and size of these modular components, the tubular chamber can be adjusted to the length of the blood vessel undergoing treatment. The introducer carries the vessel into the tubular chamber and the canula is then attached in a fluid-tight and/or pressure-limiting manner to the end of the chamber. The introducer is then removed from the open end of the tube by gently dissociating the gripping mechanism holding it to the canula, leaving the vessel in the tube secured to the canula. A syringe mechanism (1) containing treatment fluid in a reservoir is then attached to the canula so that treatment fluid can be infused through the canula, through the vessel lumen, out through the open end of the vessel, and into the space surrounding the vessel in the tubular chamber. In this manner, the vessel becomes surrounded by fluid on all sides, luminal and abluminal. A cap (6) is then fitted onto and/or into the tube, creating an enclosed space containing the vessel surrounded by treatment fluid on all sides. The vessel can remain surrounded by fluid in this manner for a proscribed duration of exposure.

Alternatively, the fluid can be pressurized using the syringe mechanism, so that the vessel is exposed to the treatment fluid in a pressurized environment, without causing any potentially harmful distension of the vessel. Such pressurization has been shown to enhance delivery of an agent to the cells of a blood vessel. A device for monitoring pressure in the fluid (10) can be incorporated into the syringe mechanism, or can be attached to the system by means of a three-way stopcock or other connection. In addition, a second syringe can be attached to the canula via a three-way stopcock, to increase the reservoir volume of the syringe mechanism. Pressurized exposure of the vessel to the treatment solution can be arrested via release of the pressure through a valve or stopcock on the cap or canula, or removal of the cap or canula from the chamber. A means of egress for the treatment fluid can also be incorporated to allow flow of the treatment fluid through the system, with or without recirculation. The system can include devices to monitor and/or regulate this flow, either manually or via an automated feedback system.

The chamber and introducer can be fashioned from materials with low coefficients of friction, including, but not limited to, slippery-surfaced fluorinated polymers, which facilitate the movement of tissue in and out of the encompassing chamber with a minimum of stretching, manipulation, and/or trauma. A low-friction surface lining the chamber also facilitates even distribution of the treatment fluid around the vessel without air trapping or bubble formation.

The system can be used to deliver a wide range of therapeutic or diagnostic agents, including, but not limited to, small molecules, macromolecules, such as proteins or nucleic acid molecules, and biological vectors, such as recombinant viral particles, for treatment of the vessel. Efficient delivery to the vessel wall can be achieved safely with a minimum of manipulation of, or trauma to, the vessel, and without wasteful excess material. Manipulation of conditions within the chamber, for example through a range of pressurization, oxygenation, and/or temperature adjustments, can also be applied.

What is claimed is:

1. A method for treating a biological tissue with a therapeutic liquid solution, said method comprising the steps of:
   (a) placing said tissue in an inner, trough-shaped introducer;
   (b) inserting the resultant trough-held tissue into a closable outer chamber;
   (c) closing said outer chamber; and
   (d) before or after step (c), infusing into said outer chamber said solution to contact said tissue with said solution.

2. The method of claim 1, wherein said biological tissue is elongate.

3. The method of claim 2, wherein said biological tissue is a blood vessel.

4. The method of claim 2, wherein, before or after step (a), one end of said tissue is secured to a canula.

5. The method of claim 4, wherein said tissue is secured to said canula by ligature.

6. The method of claim 4, wherein said canula is removably attached to said inner, trough-shaped introducer via a gripping mechanism.

7. The method of claim 4, wherein, when placed in said outer chamber with said tissue, said canula is removably attached to one end of said outer chamber.

8. The method of claim 4, wherein said therapeutic liquid solution is introduced into said outer chamber via said canula.

9. The method of claim 1, wherein, before step (c), said inner, trough-shaped introducer is removed from said outer chamber.

10. The method of claim 1, wherein said outer chamber is closed by means of a removable cap.

11. The method of claim 1, wherein said therapeutic liquid is infused into said outer chamber by means of a syringe.

12. The method of claim 1, wherein said outer chamber comprises an elongate tubular structure.

13. The method of claim 12, wherein said elongate tubular structure comprises two or more tubular segments that are reversibly hinged to one another.

14. The method of claim 13, wherein said segments are hinged so as to allow flexion between said segments.

15. The method of claim 1, wherein said therapeutic liquid solution in said outer chamber contacts said tissue under pressure.

16. The method of claim 1, wherein the interior surface of said outer chamber or the surface of said introducer onto which said tissue is placed comprises a coating having a low coefficient of friction.

17. The method of claim 1, wherein said introducer comprises a material having a low coefficient of friction.

18. The method of claim 1, wherein said outer chamber comprises a material having a low coefficient of friction.

19. An apparatus for treating a biological tissue with a therapeutic liquid solution, said apparatus comprising:
   a. a sterile outer chamber that can be closed to be fluid-tight, and that is adapted for enclosing said tissue so that it can be contacted with said solution; and b. a sterile open inner, trough-shaped introducer adapted to be inserted into said outer chamber, said introducer further being adapted to hold said tissue for introduction of the tissue into said outer chamber.

20. The apparatus of claim 19, further comprising a canula that is removably attached to said introducer via a gripping mechanism and that is adapted such that one end of an elongate tubular tissue can be removably attached to said canula.

21. The apparatus of claim 19, wherein said outer chamber comprises an elongate tubular enclosure.

22. The apparatus of claim 21, wherein said elongate tubular structure comprises two or more segments that are reversibly hinged to one another.

23. The apparatus of claim 22, wherein said segments are hinged so as to allow flexion between said segments.

24. The apparatus of claim 21, wherein, when placed in said outer chamber with said tissue and said introducer, said canula is removably attached to one end of said outer chamber.

25. The apparatus of claim 24, further comprising a cap that seals the end of said outer chamber to which said canula is not attached.

26. The apparatus of claim 19, further comprising a means for altering the pressure in said outer chamber.

27. The apparatus of claim 19, further comprising a syringe for introducing said therapeutic liquid solution into said outer chamber or for altering the pressure in said outer chamber.

28. The apparatus of claim 19, further comprising a device for monitoring the pressure within said outer chamber.

29. The apparatus of claim 19, further comprising a mechanism for automated pressurization of, or delivery of fluid into, said outer chamber.

30. The apparatus of claim 19, further comprising a feedback mechanism for regulating the pressure, fluid volume, temperature, or oxygen content of said outer chamber.

31. The apparatus of claim 19, wherein the interior surface of said outer chamber or the surface of said introducer onto which said tissue is placed comprises a coating having a low coefficient of friction.

32. The apparatus of claim 19, wherein the walls of said outer chamber are clear so that said treatment of said biological tissue can be monitored visually.

33. The apparatus of claim 19, wherein said introducer comprises a material having a low coefficient of friction.

34. The apparatus of claim 19, wherein said outer chamber comprises a material having a low coefficient of friction.

* * * * *